United States Patent
Inaka

(10) Patent No.: US 9,707,729 B2
(45) Date of Patent: Jul. 18, 2017

(54) METHOD AND APPARATUS FOR MANUFACTURING NUCLEATED TABLETS

(71) Applicant: OTSUKA PHARMACEUTICAL CO., LTD., Chiyoda-ku, Tokyo (JP)

(72) Inventor: Hiroshi Inaka, San Francisco, CA (US)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/897,453

(22) PCT Filed: Jun. 12, 2014

(86) PCT No.: PCT/JP2014/065536
§ 371 (c)(1),
(2) Date: Dec. 10, 2015

(87) PCT Pub. No.: WO2014/200046
PCT Pub. Date: Dec. 18, 2014

(65) Prior Publication Data
US 2016/0136916 A1   May 19, 2016

(30) Foreign Application Priority Data

Jun. 12, 2013 (JP) ................................ 2013-123768

(51) Int. Cl.
*B30B 11/14* (2006.01)
*A61J 3/10* (2006.01)
(Continued)

(52) U.S. Cl.
CPC ............... *B30B 11/34* (2013.01); *A61B 5/07* (2013.01); *A61J 3/10* (2013.01); *A61K 9/2095* (2013.01); *B30B 11/14* (2013.01)

(58) Field of Classification Search
None
See application file for complete search history.

(56) References Cited

U.S. PATENT DOCUMENTS 1,706,874 A   3/1929   Journo
2,214,191 A   9/1940   Batchell et al.
(Continued)

FOREIGN PATENT DOCUMENTS

EP   1925441   5/2008
EP   2251190   11/2010
(Continued)

OTHER PUBLICATIONS

International Search Report, PCT/JP2014/065536, Sep. 16, 2014.
The Extended European Search Report of European Application No. 14810504.2, dated Jan. 24, 2017, total 8 pages.

*Primary Examiner* — Mary F Theisen
(74) *Attorney, Agent, or Firm* — Hamre, Schumann, Mueller & Larson, P.C.

(57) ABSTRACT

Provided is a method and apparatus for manufacturing nucleated tablets in each of which a nucleus is positioned in a precise manner. In the tablet manufacturing machine (1), granules are charged in a mortar and then compressed by pestles while the mortar and the pestles travel along a cyclic path extending from a point and then back to the point. The path has a substantially straight path portion where the mortar and the pestles travel substantially straightly.

11 Claims, 2 Drawing Sheets

(51) Int. Cl.
    *A61K 9/20*         (2006.01)
    *A61B 5/07*         (2006.01)
    *B30B 11/34*      (2006.01)

(56) References Cited

U.S. PATENT DOCUMENTS

| | | |
|---|---|---|
| 3,724,988 A | 4/1973 | Gouws |
| 3,836,299 A * | 9/1974 | Houston .................. A01C 1/06 198/340 |
| 8,269,635 B2 | 9/2012 | Kroll et al. |
| 2003/0075830 A1 | 4/2003 | Sollich |
| 2004/0113319 A1* | 6/2004 | Kondo ...................... A61J 3/06 264/319 |
| 2010/0049012 A1 | 2/2010 | Dijksman et al. |
| 2010/0148399 A1* | 6/2010 | Gebert .................... B30B 11/14 264/299 |
| 2010/0285166 A1 | 11/2010 | Kolbe et al. |
| 2015/0164746 A1* | 6/2015 | Costello .................. A61B 5/07 264/112 |

FOREIGN PATENT DOCUMENTS

| | | |
|---|---|---|
| FR | 896061 | 2/1945 |
| GB | 191218136 | 4/1913 |
| JP | 61-54435 A | 3/1986 |
| JP | 62-178503 A | 8/1987 |
| JP | 2-243158 A | 9/1990 |
| JP | 9-206358 A | 8/1997 |
| JP | 2002-65812 A | 3/2002 |
| JP | 2011-255397 A | 12/2011 |
| JP | 2012-514798 A | 6/2012 |
| WO | 2006092683 | 9/2006 |
| WO | 2010/080765 A2 | 7/2010 |

* cited by examiner

METHOD AND APPARATUS FOR MANUFACTURING NUCLEATED TABLETS

TECHNICAL FIELD

The present invention relates to an apparatus and method for manufacturing tablets. In particular, the present invention relates to an apparatus and method for manufacturing tablets, which is preferably used in manufacturing tablets each containing IC chip or chips embedded therein.

BACKGROUND

Conventionally, various tablet manufacturing machines are disclosed in, among others, JP 2002-65812 A (Patent Document 1), JP 2011-255397 A (Patent Document 2), JP 09-206358 A (Patent Document 3), JP 02-243158 A (Patent Document 4), and JP 61-54435 A (Patent Document 5).

PRIOR ART DOCUMENT(S)

Patent Document 1: JP 2002-65812 A
Patent Document 2: JP 2011-255397 A
Patent Document 3: JP 09-206358 A
Patent Document 4: JP 02-243158 A
Patent Document 5: JP 61-54435 A Recently, attempts have been made to have patient dose tablets with an IC chip embedded therein for monitoring his or her dosing history using signals emitted from the IC chips. Examples of such tablets are disclosed, for example, in the U.S. Pat. No. 8,269,635 (Patent Document 6), the U.S. Patent Application Publication No. 2010-0049012 A (Patent Document 7), and JP 2012-514798 A (Patent Document 8).

Patent Document 6: U.S. Pat. No. 8,269,635
Patent Document 7: U.S. Patent Application Publication No. 2010-0049012
Patent Document 8: JP 2012-514798 A According to a conventional circular rotary tablet manufacturing machine, non-nucleated tablets are manufactured typically through steps of (A) charging granules into a mortar, (B) scraping off excessive granules remaining outside the mortar, (C) compressing the granules in the mortar by using associated pestles or punches, and (D) ejecting the compressed tablet from the mortar, as the mortar moves along the outer periphery of the tablet manufacturing machine. If one cyclic movement of the mortar produces only one tablet, each of the steps (A) to (D) is performed once during the cyclic movement of the mortar along the periphery of the tablet manufacturing machine. If, on the other hand, one cyclic movement of the mortar produces two or more tablets, each of the steps (A) to (D) is performed corresponding number of times during the cyclic movement of the mortar along the periphery of the tablet manufacturing machine.

The nucleated tablets are manufactured, typically, through steps of (a) charging granules into a mortar, (c) scraping off excessive granules remaining outside the mortar, (c) positioning a nucleus on the granules in the mortar, (d) charging granules on the nucleus in the mortar, (e) scraping off excessive granules remaining outside the mortar, (f) compressing the granules in the mortar by using associated pestles, and (g) ejecting the compressed tablet from the mortar, as the mortar moves along the periphery of the tablet manufacturing machine. If one cyclic movement of the mortar produces only one tablet, each of the steps (a) to (g) is performed once during the cyclic movement of the mortar around the tablet manufacturing machine. If, on the other hand, one cyclic movement of the mortar produces two or more tablets, each of the steps (a) to (g) is performed corresponding number of times during the cyclic movement of the mortar around the tablet manufacturing machine.

The rotational speed of the conventional circular rotary tablet manufacturing machine for manufacturing the non-nucleated or nucleated tablets is determined according to a process speed at the most time consuming step among steps (A)-(D) or (a)-(g). For example, the nucleus positioning step (c) in the manufacturing of the nucleated tablets can need a considerable time in positioning the nucleus supply machine with the mortar of the tablet manufacturing machine. This requires that the rotational speed of the tablet manufacturing machine is reduced to harmonize with the process speed at the step (c), which needs a longer time (tact time) for manufacturing each tablet through steps (a) to (g).

To allot suitable times for respective steps, the tablet manufacturing machine may be driven intermittently so that the most time consuming step such as step (C) is performed in an irrotational state of the machine to provide that step with a longer period of time while other steps are performed in a rotational state of the machine to provide them with respective shorter periods of time. Nevertheless, the intermittent driving requires the machine to change frequently from the rotational state to the irrotational state and vice versa, which eventually increases the tact time.

Another option may be to enlarge a radius of the circular rotary tablet manufacturing machine and thereby increase the travelling path of the mortars and, as a result, a geographical length of the time consuming step, for example, step (c). In this instance, however, the enlarged radius disadvantageously increases the size of the tablet manufacturing machine as the square of the radius.

Although the patent document 8 suggests, at paragraph 0060 and in FIG. 15 thereof, a method for manufacturing IC chip containing tablets, no detailed description is made to the structure of the manufacturing machine or the manufacturing method of the tablets.

Inventors of the present invention found that the steps of the mortar-and-pestle tablet manufacturing machine for manufacturing IC chip containing tablets need different times. For example, the step for positioning IC chip in the mortar needs longer process time, which results in a disadvantageous increase in the whole tact time The inventors also found that, according to the conventional IC chip containing tablet manufacturing process, an unwanted displacement of the supplied IC chip occurs during the movement of the associated mortar from the IC chip supply station to the subsequent granule supply station due to centrifugal force applied thereto.

To solve the problems, the invention is to provide a method and apparatus for manufacturing tablets, which is capable of shortening an overall tact time irrespective of an existence of a step which needs more than other steps and also accurately positioning the IC chip at the manufacturing of the IC chip containing tablet.

SUMMARY OF INVENTION

The tablet manufacturing machine has a mortar and pestles, the mortar and pestles being configured so that granules are charged in the mortar and then compressed by the pestles while the mortar and the pestles travel along a path extending from a point and then back to the point. The path has one or more substantially straight path portions where the mortar and the pestles travel substantially straight along the substantially straight path portion.

Preferably, an IC chip supply station is provided on the straight path portion for supplying an IC chip on the granules charged in the mortar.

Preferably, the path has a substantially ellipse or oblong shape. Also, preferably the machine is configured so that two tablets are produced by each mortar while the mortar and the pestles move from the point and then back to the point, in which the path has two opposed substantially straight path portions where the same process is performed.

A method for manufacturing tablets for supplying granules to a mortar and compressing the granules in the mortar by using associated pestles as the mortar and associated pestles move along a travel path from a position and then back to the position, comprises performing a certain process on a substantially straight path portion provided on the travel path, along which the motor and the pestles travel straightly.

Preferably, the certain process comprises at least compressing the granules in the mortar by the pestles.

Preferably, the certain process comprises at least supplying an IC chip on the granules charged in the mortar.

Preferably, the path has a substantially ellipse or oblong shape.

EMBODIMENT(S) OF THE INVENTION

Descriptions will be made to a tablet manufacturing machine and method according to the invention in connection with an exemplary embodiment for manufacturing IC chip containing tablets.

Figure 1:
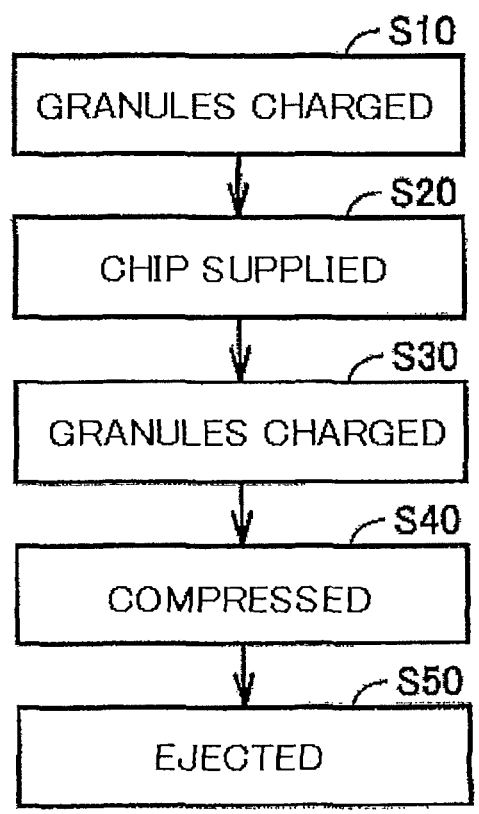
FIG. 1 is a diagram showing a series of steps in a method for manufacturing IC chip containing tablets according to the invention.

FIG. 1 is a diagram showing a series of steps in a method for manufacturing Integrated Circuit (IC) chip containing tablets according to the invention. Referring to the drawing, the exemplary nucleated tablet manufacturing process has steps of charging granules into mortars (step S10), supplying IC chips (nuclei) in the mortars (step S20), charging granules in the mortars (step S30), compressing the granules while pressing IC chips (step S40), and ejecting the tablets out of the mortars (step S50). Although not shown, a step for scraping off the granules remaining around and outside the mortars may be provided between steps S10 and S20 and/or between steps S30 and S40, as necessary.

At step S10, the granules are supplied to the mortars. The mortar is made of die. The die is made of metal and has a through-hole defined therein. A lower punch is provided in the bottom portion of through-hole to close the lower opening of the through-hole, forming a bottom-closed cavity in the die for receiving the granules charged therein. The granules may be a medicament. The granules may be compressed or may not be compressed before being charged in the cavity. If the un-compressed granules are supplied at step S10 in the cavity, a compressing step may be added to compress the granules immediately after the granules are supplied in the cavity.

At step S20, the IC chip (nucleus) is supplied in the mortar. Since the granules have been charged in the mortar in advance of step S20, the supplied chip is positioned on the granules. The chip is capable of transmitting and receiving electric or electromagnetic signal to and from an external device. For example, if the chip is designed to transmit electric signal, a receiver may be provided outside the body of patient who takes the chip containing medicament tablet. This allows the receiver to receive the electric signal from the chip within the body of patient, allowing recognition of the existence of tablet within the body of the patient.

The chip supplying step needs to place the chip in position in a precise manner. Otherwise, the chip can be seen on the exterior of the tablet, discouraging patient from dosing of the tablet. Also, an imprecise positioning of the tablet may vary a time which is required for the chip covering medicament to dissolve within the body of patient and thereby to expose the chip. The precise placement of the chip needs that substantially no centrifugal force acts on the chip during the chip supplying step. For example, if the chip is supplied into the mortar as the mortar moves along an arcuate path, it is exposed to a centrifugal force which urges the chip to displace from the position it was placed. Therefore, the chip is preferably supplied in the mortar as it is transported along a path which is substantially straight to the extent that substantially no centrifugal force would act on the chip. Of course, two or more chips may be provided to each mortar.

A feeder's chip supply operation is associated with the positioning of the mortar. Specifically, the feeder 3 drives in synchronism with the movement of the mortar so that, when a relative speed difference between the mortar and the feeder becomes substantially zero, the chip is transferred from the feeder to the mortar. A detector may be provided to detect a position of the mortar so that, if it is determined that the mortar reaches a predetermined position, a computer transmits a signal to activate the feeder for supplying the chip. Preferably, a path from the chip storage within the feeder to the mortar to which the chip should be supplied is as short as possible, because the longer path increases the IC chip supply time and, as a result, decreases the production efficiency. Also, to prevent less or more number of chips, different from the predetermined number, from being supplied to the mortar, a detector may be provided on the path to detect the number of chips passed by and, if it is determined that less or more number of chips have been supplied to the mortar, the tablet manufacturing machine is halted. This allows that the excessive number of chips supplied to the mortar are readily removed therefrom. Further, by analyzing images captured in the process for supplying chip or chips to the mortar, a determination may be made to whether the chip or chips have been placed at substantially the central region of the mortar.

Preferably, the mortar is transported in a horizontal surface as it is supplied with the chip.

At step S30, the mortar is supplied with granules. The granules supplied at this step may be the same as or different from those supplied at step S10. The granules may be compressed or may not be compressed before being supplied to the mortar. An additional step may be provided to scrape off the granules remaining around and outside the mortar so that a predetermined amount of granules is filled in the die.

At step S40, the granules charged in the mortar are compressed with the movement of the upper punch into the mortar through the upper opening of the mortar as the lower punch is stationary positioned in the mortar to close the lower opening of the mortar. This causes the granules to be compressed between the upper and lower punches to produce the tablet. The compressing step may have a first sub-step for removing air from the mortar and a second sub-step for compressing the mass of granules into a predetermined thickness.

At step S50, the resultant tablet compressed at the compressing step is ejected from the mortar. The tablet may be ejected by moving the upper punch out of the mortar and then moving the lower punch upward to eject the tablet upward or by moving the lower punch out of the mortar and then moving the upper punch downward to eject the tablet downward.

Figure 2:
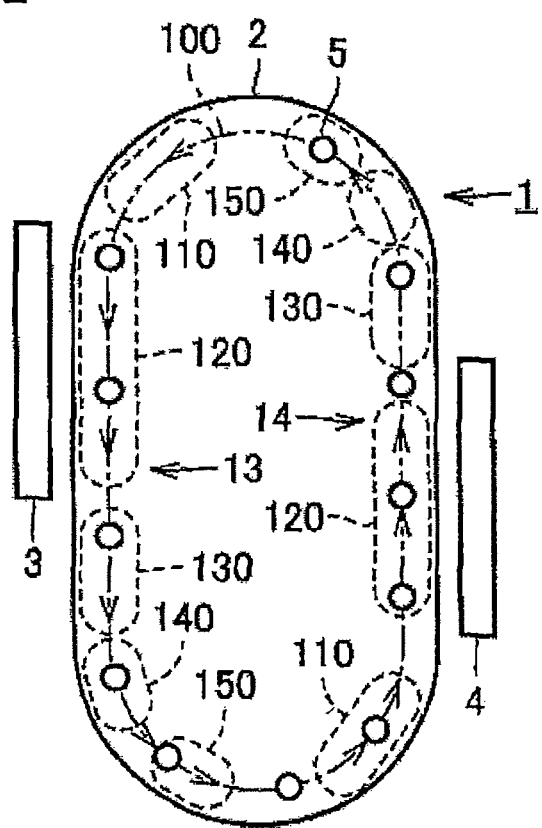
FIG. 2 is a top plan view showing a movement of mortars in the tablet manufacturing machine according to the invention.

FIG. 2 is a top plan view showing a travel path of the mortars in the tablet manufacturing machine. Referring to the drawing, the tablet manufacturing machine 1 has an ellipse or oblong shaped table 2. The table 2 supports a plurality of mortars 5 so that the mortars 5 can move along the periphery of the table 2 along a travel path 100. The travel path 100 is a cyclic path so that each mortar 5 cyclically travels along the periphery of the table 2.

The tablets are produced while the mortars travel along the path 100. Specifically, the granules are charged in the mortar 5 (step S10) at the granule charge station 110. Next, the IC chip or chips are placed on the granules charged in the mortar 5 (step S20) at the chip supply station 120. Then, the above-described steps S30, S40, and S50 are performed at the granule charge station 130, the compress station 140, and the eject station 150, respectively.

According to the tablet manufacturing machine shown in FIG. 2, each mortar produces two tablets during one cyclic travelling of the die 5. During the travelling, the most time consuming step, i.e., the chip supply step (S20), is performed at opposing linear path portions.

As described above, the exemplary tablet manufacturing machine 1 is designed so that the mortars 5 travel along the oblong path, not circular path, and the time consuming step (S20) is positioned at the straight path portions. This allows the mortars 5 to be transported at a constant speed during the entire tablet manufacturing process, without any need to reduce the travelling speed of the mortars or intermittently halt the travelling of the mortars, which shortens the tact time in which the tablet is produced.

Also, substantially no centrifugal force acts on the mortars 5 moving past the chip supply station, which prevents the disadvantageous displacement of the chips.

Further, although the granule supply unit is typically positioned separately from the tablet manufacturing machine, the oblong tablet manufacturing machine defines a wide space at the center of the tablet manufacturing machine, which may be used for the positioning of the granule supply unit, which results in a compact tablet manufacturing machine.

Although the mortars 5 are transported on a horizontal plane in the previous embodiment, they may be transported in a non-horizontal plane or curved plane. For example, portions of the mortar travel path positioned on the upstream and/or downstream side of the supply stations 3 and 4 with respect to the travelling direction of the mortars may be positioned above or below the portions of the mortar travel path adjacent the chip supply stations 3 and 4.

Although the table 2 has the oblong configuration with two linear travel path portions 13 and 14 in the previous embodiment, it is not limited thereto and may have a substantially rectangular configuration on which the mortars 5 are transported. Also, the straight travel path portions need not to be strictly straight and it may be arched to the extent that a centrifugal force does not adversely affect the positioning of the chips. In sum, the tablet manufacturing machine may have another configuration such as triangle or polygonal shape provided that it has straight travel path.

Although the IC chip supply process is performed while the mortars are being transported on the straight travel path portions because the IC chip supply is the most time consuming process, if a certain step (for example, compressing step) consumes more time than others, the certain step is preferably performed as the mortar moves along the straight travel path portion.

The invention is not limited to the manufacturing of the IC chip containing tablets and it may be applied to the manufacturing of the nucleated or non-nucleated tablets.

It should be noted that the above disclosed embodiments are exemplary and not restrictive. Also, the scope of the invention should be defined by the appended claims, not by the above descriptions, and each and every improvement and modification is intended to be included within the scope of the claims and the equivalents thereof.

The present invention is applicable to a method and apparatus for manufacturing tablets.

PARTS LIST

1: tablet manufacturing device
2: table
3,4: chip supply station
5: mortar
13, 14: straight path portion
100: travel path
110: granule supply station
120: chip supply station
130: granule supply station
140: compress station
150: eject station

The invention claimed is:

1. A tablet manufacturing machine, comprising:
a mortar and associated pestles, the mortar and pestles being configured so that granules are charged in the mortar and then compressed by the pestles while the mortar and the pestles travel along a path extending from a point and then back to the point,
the path including at least one substantially straight path portion where the mortar and the pestles travel in a substantially straight direction along the substantially straight path portion, and
a nucleus supply station provided on the substantially straight path portion and configured to supply a nucleus on the granules charged in the mortar.

2. The tablet manufacturing machine of claim 1, wherein the path has a substantially oblong shape.

3. The tablet manufacturing machine of claim 2, wherein the machine is configured so that two tablets are produced using the mortar while the mortar and the pestles move from the point and then back to the point, and
wherein the path has two opposed substantially straight path portions where the same process is performed.

4. The tablet manufacturing machine of claim 1, wherein the path includes a first granule charge station configured to charge first granules in the mortar, the nucleus supply station, a second granule charge station configured to charge second granules on the nucleus, and a compress station configured to compress the first and second granules in the mortar by the pestles to form a tablet, in this order,
wherein the nucleus supply station is provided in the substantially straight path portion.

5. The tablet manufacturing machine of claim 4, wherein the second granule charge station is provided in the substantially straight path portion.

6. The tablet manufacturing machine of claim 1, wherein the path has a substantially oblong shape including two substantially straight path portions, each of the two substantially straight path portions including a granule charge station configured to charge granules in the mortar, and a nucleus supply station configured to supply a nucleus on the granules charged in the mortar.

7. The tablet manufacturing machine of claim 1, wherein the nucleus is an IC chip.

8. A method for manufacturing tablets for supplying granules to a mortar and compressing the granules in the mortar by using associated pestles as the mortar and associated pestles move along a path from a position and then back to the position, comprising:

performing a certain process on a substantially straight path portion provided on the path, along which the mortar and the pestles travel in a substantially straight direction, wherein the certain process comprises supplying a nucleus on the granules charged in the mortar.

9. The method of claim 8, wherein the certain process further comprises compressing the granules in the mortar by the pestles.

10. The method of claim 8, wherein the path has a substantially oblong shape.

11. The method of claim 8, wherein the nucleus is an IC chip.

* * * * *